United States Patent [19]
Mauldin

[11] Patent Number: 5,856,260
[45] Date of Patent: Jan. 5, 1999

[54] PREPARATION OF HIGH ACTIVITY CATALYSTS; THE CATALYSTS AND THEIR USE

[75] Inventor: Charles H. Mauldin, Baton Rouge, La.

[73] Assignee: Exxon Research and Engineering Company, Florham Park, N.J.

[21] Appl. No.: 845,015

[22] Filed: Apr. 22, 1997

[51] Int. Cl.$^6$ .............. B01J 23/00; B01J 23/72; B01J 23/56; B01J 23/70
[52] U.S. Cl. .............. 502/325; 502/331; 502/332; 502/338; 502/345; 502/514; 502/506; 502/172; 518/700
[58] Field of Search .............. 502/325, 331, 502/336, 338, 345, 514, 506, 172; 518/700

[56] References Cited

U.S. PATENT DOCUMENTS

| | | | |
|---|---|---|---|
| Re. 31,037 | 9/1982 | Inooka et al. | 252/57 |
| 4,234,462 | 11/1980 | Bondar et al. | 252/463 |
| 4,764,498 | 8/1988 | Wissner et al. | 502/251 |
| 4,801,573 | 1/1989 | Eri et al. | 502/302 |
| 4,977,126 | 12/1990 | Mauldin et al. | 502/242 |
| 5,064,803 | 11/1991 | Nunan | 502/170 |
| 5,468,709 | 11/1995 | Yamaguchi et al. | 502/210 |

FOREIGN PATENT DOCUMENTS

| | | | |
|---|---|---|---|
| 0601722 | 6/1994 | European Pat. Off. | C10G 45/08 |

Primary Examiner—Gary Geist
Assistant Examiner—Jafar Parsa
Attorney, Agent, or Firm—Jay Simon

[57] ABSTRACT

A process for the preparation of a catalyst useful for conducting carbon monoxide conversion reactions, especially a Fischer-Tropsch catalyst, use of the catalyst for conducting such reactions, especially Fischer-Tropsch reactions, and the composition produced by said process. In the preparation of the catalyst, a solution of a polyol is employed to impregnate and disperse a compound or salt of a catalytic metal, or metals, e.g., copper or an Iron Group metal such as iron, cobalt, or nickel, or in a preferred embodiment both a compound or salt of rhenium and a compound or salt of a catalytic metal, or metals, e.g., copper or an Iron Group metal such as iron, cobalt, or nickel onto a refractory inorganic oxide support, e.g., titania. The rhenium, when present only in small amount permits full and complete reduction of the catalytic metal, or metals, dispersed by the polyol. Higher catalyst activities with lower rhenium loadings are thus achieved than in previous preparations where higher concentrations of rhenium were required to both effectively disperse, and reduce the catalytic metal, or metals, during the preparation. Surprisingly, as little as about $1/10$ of the rhenium is required to accomplish the reduction promotion where the dispersion is effected with the polyol.

20 Claims, No Drawings

PREPARATION OF HIGH ACTIVITY CATALYSTS; THE CATALYSTS AND THEIR USE

FIELD OF THE INVENTION

This invention relates to a process, or method, for the production of a high activity catalyst by dispersion of a catalytic metal, or metals, particularly copper or an Iron Group metal, notably cobalt, or both a catalytic metal and rhenium onto a refractory inorganic oxide support, notably titania; the catalyst; its reduction, and use of the catalyst for conducting carbon monoxide hydrogenation reactions, especially Fischer-Tropsch reactions.

BACKGROUND

Carbon monoxide hydrogenation reactions are well known. For example, Fischer-Tropsch synthesis processes, or processes for the catalytic conversion of synthesis gas, i.e., a mixture of hydrogen and carbon monoxide, to high quality distillate fuels or mixtures of $C_5+$ liquid hydrocarbons are well known. For example, the Group VIII non-noble metals, iron, cobalt, and nickel have been widely used to catalyze Fischer-Tropsch reactions, and these metals have been deposited on various supports, and promoted with various other metals. In U.S. Pat. No. 4,568,663, e.g., there is disclosed a process of this type which utilizes a highly active catalyst composition constituted of cobalt-rhenium-titania, Co—Re—$TiO_2$. This catalyst is made, e.g., by impregnating a concentrated aqueous solution of cobalt nitrate and perrhenic acid onto a titania support by the conventional incipient wetness method, drying, and then calcining to decompose the nitrate salt to the oxide. Several important functions are served by the rhenium. A major function is served by rhenium during the calcination of the catalyst, during which cobalt nitrate decomposes to cobalt oxide, in that it causes the cobalt oxide to become more highly dispersed. It also preserves the cobalt oxide in highly dispersed state under high temperature oxidizing conditions, such as is found useful for regenerating cobalt catalysts. It is also a function of the rhenium to lower the temperature of the reduction of cobalt oxide to the zero valence state, which is required to achieve full activity. Rhenium makes it easier to more fully reduce the cobalt. High dispersal, and full reduction of the cobalt results in a more active catalyst. This result however does not come without cost, for rhenium is a relatively expensive commodity. Thus, there exists a need for means to better disperse the cobalt with a lesser amount of rhenium, find means for recovering the rhenium, or find other more available, less expensive materials for promoting the dispersion, and reduction of the metals.

SUMMARY OF THE INVENTION

The present invention, which meets this and other needs, relates to a novel process for the preparation of a catalyst useful for the hydrogenation of carbon monoxide, especially to a Fischer-Tropsch catalyst, the catalyst, and process for the use of this catalyst for conducting such reactions, especially Fischer-Tropsch synthesis reactions, i.e., reactions for the production of $C_5+$ liquid hydrocarbons from hydrogen and carbon monoxide. In the preparation of the Fischer-Tropsch catalyst, a preformed particulate refractory inorganic solids support is impregnated with (a) a compound, or salt, of a catalytic metal, or metals, suitably copper or an Iron Group metal and (b) a polyol or polyhydric alcohol. And preferably, a preformed particulate refractory inorganic solids support, preferably titania, is impregnated with (a) a compound, or salt, of a catalytic metal, or metals, suitably copper or an Iron Group metal, (b) a polyol, or polyhydric alcohol, and (c) a compound, or salt, of rhenium. In impregnating the support, the support is contacted, preferably, with a single solution containing both (a) and (b), or all of (a), (b), and (c), respectively. The polyol is sufficient to distribute the compound or salt of the catalytic metal, copper or Iron Group metal in highly dispersed form, onto the support; and, the rhenium, when added, is sufficient to produce full reduction of the dispersed metal. Whereas rhenium has been used in the past to produce both of these functions, a far lesser amount of rhenium is required to produce both dispersion and reduction of the metal when the rhenium is used in conjunction with the polyol.

Polyols useful in the practice of this invention are characterized as molecules containing straight carbon chains, at least two carbon atoms of which bears a hydroxyl group; the preferred polyols having the following empirical formula:

$$C_nH_{2n+2}O_x$$

where n is an integer ranging from 2 to about 6, and x is an integer ranging from 2 to n. In other words, n is 2, 3, 4, 5 or about 6, and $2 \leq x \leq n$ this including such polyols as 2,3-dihydroxybutane, 2,3,4-trihydroxypentane, 2,2dihydroxyhexane, 2,2,4-trihydroxyhexane, and including more preferably the sugar alcohols; most preferably those alcohols having the formula $$HOCH_2—(CHOH)_{n'}—CH_2OH$$

where n' is an integer defining the number of CHOH groups, or groups in a straight chain of carbon atoms each of which bears a hydrogen and a hydroxyl group, n' ranging from 0 to about 4, and more preferably from about 2 to about 4. Exemplary of polyhydric alcohols, or polyols, useful in the practice of this invention are glycol, a dihydric alcohol; glycerol, a trihydric alcohol; tetritols such as erythritol, threitol, and the like; pentitols, such as ribitol, arabinitol, xylitol, and the like; and hexitols, such as allitol, dulcitol, gluciotol, sorbitol, mannitol, and the like.

It has been found that the copper or Iron Group metal can be more effectively dispersed onto the support via use of the polyol than with rhenium, as a consequence of which no rhenium is required to effect a full, and complete dispersion of the catalytic metal, or metals. However, some rhenium is generally useful, and sometimes required since its presence enables a more complete and full reduction of the dispersed copper or Iron Group metal to the zero valent state. Accordingly, in the preferred practice of this invention, a small amount of a compound or salt of rhenium, and both a compound or salt of copper or an Iron Group metal and a polyol are employed to disperse the copper or Iron Group metal, and rhenium, into the solids support component of the catalyst during the impregnation; dispersion of the copper or Iron Group metal into the preformed catalyst resulting from the presence of the polyol, while the rhenium is effective in permitting full reduction of the catalyst after calcination. The copper or Iron Group metal compound, and rhenium compound, are thus effectively dispersed during the impregnation step, and during calcination the polyol is removed by combustion leaving behind crystallites of well dispersed oxides of the copper or Iron Group metal and the rhenium. Essentially complete reduction of the crystallites of the metals is achieved on contact of the calcined catalyst with a reducing agent, e.g., hydrogen. Surprisingly, in the preparation of a catalyst it is found that considerably less rhenium is required overall when prepared with a polyol to produce a full, similar level of activity in a reduced copper or Iron Group metal/rhenium catalyst of given composition, used in a carbon monoxide hydrogenation or Fischer-Tropsch reaction, than with a reduced catalyst of corresponding composition, used in a similar carbon monoxide hydrogenation or Fischer-Tropsch reaction at similar process conditions, made in a preparation otherwise similar except that the catalyst was made without use of a polyol.

DETAILED DESCRIPTION

The catalysts are formed by deposition of the catalytic metal, or metals, on a previously pilled, pelleted, beaded, extruded, spray dried, or sieved support material by the impregnation method. In preparing the catalysts, the metals are deposited from solution on the support in preselected amounts to provide the desired absolute amounts, and weight ratios of the metals being deposited. Catalysts constituted of cobalt and rhenium supported on titania, or a titania-containing support, silica, etc. with or without the addition of an additional metal, or metals, promoter or modifier, e.g., ruthenium, hafnium, zirconium, titanium, chromium, thoria, copper, etc., exhibit superior hydrocarbon synthesis characteristics and provide high selectivities in the conversion of synthesis gas to $C_5+$ hydrocarbon liquids. Suitably, the metals are codeposited by contact and treatment of the support with a solution, suitably an aqueous solution, which contains the polyol, e.g., sorbitol, in addition to the compound or salt of the copper or Iron Group metal, e.g., cobalt, or the compound or salt of the rhenium, or both the compound or salt of the copper or Iron Group metal and the compound or salt of the rhenium.

The catalytic metal, copper or Iron Group metal, and the rhenium can be deposited from solution in sequence, or codeposited from the same impregnating solution, and the polyol can be deposited from solution in sequence with the copper or Iron Group metal, and rhenium, or codeposited with the copper or Iron Group metal and the rhenium. The polyol can thus be codeposited with a catalytic metal, or metals, or it can be deposited from solution by a separate impregnation. Preferably however, the polyol is codeposited with the copper or Iron Group metal and the rhenium. The volume of impregnating solution used in an impregnation usually ranges from about 1 to about 20 times the volume of the support, and is generally carried out at ambient or elevated temperature. Preferably, the impregnation is carried out at conditions of incipient wetness, and at essentially ambient temperature. In accordance with the incipient wetness technique, as is known, the volume of the impregnating solution and amount of metals is predetermined to correspond to the maximum volume which will just fill the internal pore volume of the support, with no liquid in excess on impregnation of the support. Various refractory inorganic oxide supports are useful in the formaton of catalysts pursuant to the practice of this invention. Exemplary of such supports are titania, which is preferred, silica, silica-alumina, alumina, and the like.

Highly concentrated metal salt solutions are most desirable for preparing hydrocarbon synthesis catalysts because they generate the highest metal loading per impregnation, higher metal loadings leading in turn to higher catalytic activity. Common salts or compounds of the catalytic metals can generally be used. However, it has been found that the nitrate salt, especially in the case of cobalt is preferred because it is the most readily available and least expensive salt and, more importantly, it possesses the highest degree of solubility in water. Cobalt acetate is also suitable, although it is less water soluble. Cobalt chloride and sulfate are not suitable for making hydrocarbon synthesis catalysts, presumably because of poisoning by residual anions not removed in the calcination, regardless of the promotion of dispersion by polyols. Solvents other than water may be used, e.g., alcohols, ketones and the like, but these solvents are generally not preferred because of lower metal salt solubility and added manufacturing cost. Suitable rhenium compounds are the common water soluble species, especially perrhenic acid and ammonium perrhenate.

The catalytic metal, copper or Iron Group metal, preferably the latter, and more preferably cobalt, is added to the support in amount sufficient to provide from about 2 percent to about 50 percent, preferably from about 5 percent to about 35 percent of the elemental metal, based on the total weight of the finished catalyst (wt. %: dry basis). The maximum metal loading that can be obtained per impregnation will depend upon the support pore volume, which will in turn depend upon the support composition, and the metal concentration in the impregnating solution. Multiple impregnation/calcination steps may be used to obtain high final metal loadings. Other metals, e.g., thorium, cerium, hafnium, uranium and the like can be added if desired to modify or promote the activity of the finished catalyst. These metals when present are added in weight ratio to copper or Iron Group metal ranging above about 0.01:1, preferably from about 0.025:1 to about 0.1:1. Rhenium is added to the support in concentration sufficient to provide a weight ratio of elemental rhenium:elemental copper or Iron Group metal (e.g., Re/Co weight ratio) in the finished catalyst ranging from about 0.005:1 to about 0.2:1, preferably from about 0.01:1 to about 0.1:1 (dry basis). The polyol is added to the impregnating solution in concentration ranging from about 2 percent to about 20 percent, preferably from about 6 percent to about 15 percent, based on the weight of the total solution; and the solution is contacted with the support to disperse the metal compound, or compounds, onto the support. In such treatment it disperses the metal, or metals, onto the support even more effectively than the rhenium. The catalyst, after impregnation, is dried by heating, suitably at temperatures ranging from about 30° C. to about 120° C., in an air, nitrogen or other gas stream or under vacuum. The metals are converted to an oxide form by calcination, suitably at temperature ranging from about 200° C. to about 550° C., preferably from about 250° C. to about 400° C., and the polyol is burned, combusted, and removed from the catalyst. The catalyst is then activated by reduction, suitably by contact with hydrogen at temperature ranging from about 250° C. to about 550° C., preferably from about 275° C. to about 425° C., for periods ranging from about 0.5 hour to about 24 hours at pressures ranging from above ambient to about 40 atmospheres.

The catalyst produced in accordance with this invention, particularly those comprised of the Iron Group metals, corresponds in composition to those known, and useful in the conversion of synthesis gas to $C_5+$ hydrocarbons. The Fischer-Tropsch, or hydrocarbon synthesis process is carried out at temperatures of about 160° C. to about 325° C., preferably from about 190° C. to about 260° C., pressures of about 5 atm to about 100 atm, preferably about 10–40 atm and gas hourly space velocities of from about 300 V/Hr/V to about 20,000 V/hr/V, preferably from about 500 V/hr/V to about 15,000 V/hr/V. The stoichiometric ratio of hydrogen to carbon monoxide in the synthesis gas is about 2.1:1 for the production of higher hydrocarbons. However, $H_2$/CO ratios of 1:1 to about 4:1, preferably about 1.5:1 to about 2.5:1, more preferably about 1.8:1 to about 2.2:1 can be employed. These reaction conditions are well known and a particular set of reaction conditions can be readily determined by those skilled in the art. The reaction may be carried out in virtually any type reactor, e.g., fixed bed, moving bed, fluidized bed, slurry, bubbling bed, etc. The waxy, or paraffinic product from the F-T reactor, or reactor utilizing the catalyst made pursuant to the practice of this invention is an essentially non-sulfur, non-nitrogen, non-aromatics containing hydrocarbon. It is a liquid which can be produced and shipped from a remote area to a refinery site for further chemically reacting and upgrading to a variety of products, or produced and upgraded at a refinery site. Separator products from an F-T reactor, i.e., hot separator and cold separator liquids, respectively, i.e., $C_4$-$C_5$ hydrocarbons, constitute high quality paraffin solvents which, if desired, can be hydrotreated to remove olefin impurities, or employed without hydrotreating to produce a wide variety of wax products. The reactor wax, or $C_6+$ liquid hydrocarbons from the F-T reactor, on the other hand, can be upgraded by various hydroconversion reactions, e.g., hydrocracking, hydroisomerization catalytic dewaxing, isodewaxing, etc. or combinations thereof, to produce such products as stable, environmentally benign, non-toxic mid-distillates, diesel and jet fuels, e.g., low freeze point jet fuel, high cetane jet fuel, etc. isoparaffinic solvents, lubricants, e.g., lube oil blending components and lube oil base stocks suitable for transportation vehicles, non-toxic drilling oils suitable for use in drilling muds, technical and medicinal grade white oil, chemical raw materials, and various specialty products.

The following non-limiting examples, and comparative demonstrations, exemplify the more salient and preferred embodiments of the invention.

EXAMPLES

A series of catalysts were prepared by impregnating a support, generally a rutile or anatase titania support, and silica, with a concentrated aqueous solution of cobalt nitrate and perrhenic acid via the incipient wetness technique. In most of the preparations, as tabulated hereafter, different polyols were dissolved in cobalt nitrate/perrhenic acid solutions, the polyol generally being added in greater than 10 wt. % concentration in the impregnating solution. The amount of water present in each impregnating solution was adjusted for the weight of the polyol added to maintain a nearly constant 15 wt. % cobalt, calculated as elemental cobalt, in the solution. In base case preparations, for comparative purposes, no polyol was added to the cobalt nitrate/ perrhenic acid solution. In some cases the catalysts were made by single impregnations (about 7 wt. % Co in the finished titania supported catalysts) in the exploration of preparation variables. In other cases, a second impregnation was applied to increase metals loadings and produce finished catalysts more typical of those which may be employed in large scale operations. In each preparation, after impregnation the catalyst was dried and then calcined in air to decompose the nitrate salt to the oxide and burn off the organic additive.

Most of the preps were made with a spray-dried titania support. Two batches were used which were obtained by calcining the raw spray-dried support at two different temperatures, as indicated in the following table. A spray-dried silica support was also used in a few examples.

| Designation | Calcination Temp. °C. | Surface Area $m^2/g$ | $H_2O$ Pore Volume, cc/g |
|---|---|---|---|
| Rutile[1] | 1000 | 19 | 0.33 |
| Anatase[2] | 500 | 29 | 0.50 |
| Silica | 800 | 170 | 1.02 |

[1] 94% Rutile - 6% Anatase $TiO_2$
[2] 27% Rutile - 73% Anatase $TiO_2$

The catalysts were characterized by the following tests.

$O_2$ Chemisorption: measured with $O_2$ pulses in helium at 25° C. after reduction in hydrogen at 450° C. Results are expressed as micromoles $O_2$ per gram and as an O/Co atomic ratio. The oxygen chemisorption is a measure of the relative dispersion of cobalt oxide on the support.

Fixed Bed Hydrocarbon Synthesis (HCS) Test: conducted at 200° C., 280 psig, with a syn gas feed of $64H_2$—32CO—4Ne and space velocity adjusted as required to give conversion around 70% at 20 hours on stream. Catalysts were diluted with 1–7 parts by volume of titania to minimize temperature gradients in a 0.25 inch ID reactor, used to conduct the test. Prior to introducing the syn gas, the catalyst is reduced in situ in hydrogen for one hour at 450° C. Conversion of CO and selectivity to methane (mole % of CO converted to $CH_4$) are shown in Table 2. Values for "Cobalt Productivity," which has the units of liters of CO converted per hour per gram of cobalt, are also included in Table 2.

Table 1: Effect of Polyols As Dispersion Aids

Table 1, Examples 2–5, summarizes the results obtained with different polyols as impregnation aids for dispersing cobalt throughout a support. Example 1 is a control; no polyol having been added to the impregnating solution. All of Examples 1–5 were made with the rutile titania support, without having added any rhenium promoter. The key results are given in the second to last column, i.e., reference being made to the O/Co chemisorption data. The catalysts are grouped according to the length of the longest carbon chain in the polyol, or organic used as a dispersing aid. Example 1, as indicated, demonstrates for comparative purposes a run made without use of any polyol in the preparation. Example 2 shows no improvement when the catalysts are produced by dispersion of the cobalt with polyvinyl alcohol. In Examples 3–5, on the other hand, wherein glycerol and sorbitol, respectively, were used in the preparations, higher relative dispersions were obtained. These alcohols give O/Co values ranging from 0.360 to 0.546 compared to values of less than 0.3 for the base case and the run made with the polyvinyl alcohol. From a list of the structures of the polyols tested, the critical structural features of the preferred polyols are shown to have a total carbon chain of at least 3 atoms, preferably 5 atoms. The polyols, it is believed, improve cobalt dispersion by covering the titania surface with a thin "blanket" of the polyol, which provides a trap for molten anhydrous cobalt nitrate as it is generated in the pores during the drying/calcination process. In the absence of something so polar to bind to, the cobalt salt probably coalesces into larger crystallites as it decomposes to the oxide.

In Examples 6–14 both cobalt and rhenium were impregnated onto an anatase titania support. Example 6 is employed as a control. No polyol was added to the solution in this run to impregnate the anatase titania support. Examples 7–14, on the other hand, give the results obtained when different hydroxyl-containing compounds, or polyols were added to the impregnating solution to impregnate both cobalt and rhenium into the anatase titania support. In these runs, comparing the O/Co ratios of Examples 6 and 7, it was found that the 1,2-hexanediol was ineffective; and although the O/Co ratio of the catalysts was improved with the use of the 1,6hexanediol and 1,2,6-trihydroxyhexane, respectively, an exotherm developed when drying the catalysts that damaged the catalysts. It is believed that this reaction developed as the result of an oxidation reaction, and may be avoided by use of a water soluble cobalt compound other than cobalt nitrate, e.g., cobalt acetate. On the other hand, all O/Co values obtained in Examples 10–14, which used preferred polyols as impregnation aids, were for the most part considerably higher than in the base case.

Impregnation of a silica support with an impregnation solution containing increasing concentrations of sorbitol as the dispersing aid, to disperse cobalt and rhenium onto the support (Examples 16–18) vis-a-vis the control which contained no dispersing aid (Example 15) likewise shows increasing O/Co ratios.

in the case of silica, are processes that are favored by higher temperature which counteract any positive gains in reduction.

A series of four runs were made with each of the catalysts produced in the preparations described by reference to Examples 15–18; the catalyst of Example 15 being that used for the run described in Example 19; the catalyst of Example 16 being that used for the run described in Example 20; the catalyst of Example 17 being that used for the run described in Example 21, etc. Example 19 is a control; no polyol having been used to impregnate the rhenium and cobalt into the silica support. In each of Examples 20–22 however sorbitol was used in the impregnating solution in gradually increased concentration. The Cobalt Productivity of the catalysts, as will be observed, shows a rapid improvement, i.e., from 2.66 (Example 19) to 3.55 (Example 20), and with

TABLE 1

Polyols As Dispersion Aids

| Example (Cat. #) | Support | Organic | Wt % Polyol in impreg soln* | Polyol/Co mol ratio | Wt % Co | Wt % Re | $O_2$ Chemis | O/Co | Exotherm in drying |
|---|---|---|---|---|---|---|---|---|---|
| 1 | Rutile $TiO_2$ | None | 0 | 0 | 7.06 | 0 | 165 | 0.276 | |
| 2 | Rutile $TiO_2$ | Polyvinyl Alcohol | 1 | — | 6.78 | 0 | 154 | 0.268 | |
| 3 | Rutile $TiO_2$ | Glycerol | 7.2 | 0.306 | 7.3 | 0 | 223 | 0.360 | |
| 4 | Rutile $TiO_2$ | Glycerol | 10.4 | 0.444 | 7.3 | 0 | 261 | 0.422 | |
| 5 | Rutile $TiO_2$ | Sorbitol | 10.4 | 0.224 | 7.28 | 0 | 337 | 0.546 | |
| 6 | Anatase $TiO_2$ | none | 0 | 0 | 10.2 | 0.433 | 391 | 0.452 | |
| 7 | Anatase $TiO_2$ | 1,2-Hexanediol | 11 | 0.368 | 7.45 | 0.351 | 236 | 0.374 | Yes |
| 8 | Anatase $TiO_2$ | 1,6-Hexanediol | 11 | 0.368 | 9.69 | 0.437 | 574 | 0.699 | Yes |
| 9 | Anatase $TiO_2$ | 1,2,6-Trihydroxyhexane | 11 | 0.324 | 9.92 | 0.423 | 500 | 0.595 | Yes |
| 10 | Anatase $TiO_2$ | Ethylene Glycol | 11 | 0.7 | 9.72 | 0.458 | 569 | 0.691 | |
| 11 | Anatase $TiO_2$ | Glycerol | 11 | 0.472 | 10 | 0.467 | 631 | 0.745 | |
| 12 | Anatase $TiO_2$ | Erythritol | 11 | 0.356 | 10.3 | 0.477 | 601 | 0.689 | |
| 13 | Anatase $TiO_2$ | Arabitol | 11 | 0.286 | 10.3 | 0.444 | 613 | 0.702 | |
| 14 | Anatase $TiO_2$ | Sorbitol | 11 | 0.238 | 10.1 | 0.454 | 610 | 0.713 | |
| 15 | $SiO_2$ | none | 0 | 0 | 17.4 | 0.77 | 776 | 0.526 | |
| 16 | $SiO_2$ | Sorbitol | 6.5 | 0.14 | 18.1 | 0.8 | 940 | 0.613 | |
| 17 | $SiO_2$ | Sorbitol | 11.5 | 0.247 | 18.1 | 0.8 | 1749 | 1.140 | |
| 18 | $SiO_2$ | Sorbitol | 15.6 | 0.337 | 18.1 | 0.8 | 1452 | 0.947 | |

*15 wt % Co in solution

Table 2: Hydrocarbon Synthesis Tests With Co—Re—$SiO_2$ Catalysts

The incorporation of some rhenium permits maximization of the hydrocarbon synthesis activity of the catalyst. The polyols function well in generating cobalt dispersion, but the activity of the catalyst does not correspondingly increase until the cobalt oxide is reduced to the active zero-valent state. Simply applying higher temperature in the reduction step does not improve the activity because the growth of a titania overlayer with titania, or sintering of the cobalt metal the introduction of sorbitol as a dispersing aid, up to 5.16 (Examples 21, 22).

While Cobalt Productivity is very useful in assessing cobalt effectiveness in the hydrocarbon conversion reaction, Weight Productivity is the activity measure that best defines the relative performance of a catalyst in a slurry reactor. Weight Productivity results (cc CO converted per hour per gram of catalyst) for Examples 19–22 show that the higher metal loading obtained with the silica support is significant.

TABLE 2

Hydrocarbon Synthesis Tests With Co—Re—$SiO_2$ Catalysts

| Example (Run #) | Wt % Co | Wt % Re | Organic | % org in soln | GHSV | CO Conv | Mol % $CH_4$ | Co Prod | Wt Prod |
|---|---|---|---|---|---|---|---|---|---|
| Run Conditions: 200 C, 280 psig, 64% $H_2$-32% CO-4% Ne, 20 hr data, 0.567 g/cc cat density, reduced in $H_2$ 450 C-1 hr. | | | | | | | | | |
| 19 | 17.4 | 0.77 | none | 0 | 2000 | 41 | 7.4 | 2.66 | 463 |
| 20 | 18.1 | 0.8 | Sorbitol | 6.5 | 2000 | 57 | 6.5 | 3.55 | 643 |
| 21 | 18.1 | 0.8 | Sorbitol | 11.5 | 2400 | 69 | 7 | 5.16 | 935 |
| 22 | 18.1 | 0.8 | Sorbitol | 15.6 | 2400 | 69 | 7.3 | 5.16 | 935 |

Complete reduction of the catalytic metal, or metals, is required to achieve full catalyst activity. Full catalyst activity however can be achieved by only a small amount of rhenium, even at lower reduction temperatures. Surprisingly, as little as 1/10 of the base case amount of rhenium will satisfactorily promote the reduction when the dispersion is accomplished by the presence of the polyol. The copresence of the polyol with the rhenium allows drastic reductions in the amount of rhenium employed while yet achieving full dispersion and reduction of the catalyst.

Having described the invention, what is claimed is:

1. A process for forming a catalyst useful for the hydrogenation of carbon monoxide which comprises
   impregnating a refractory inorganic oxide support by contact with a solution which contains
   a) a compound, or salt, of a catalytic metal, or metals,
   b) a polyol having the following empirical formula $C_n H_{2n+2} O_x$ where n is an integer ranging from 2 to about 6, and x is an integer ranging from 2 to n, sufficient to disperse the compounds or salt of the catalytic metal, or metals, onto the support, and
   drying, and removing the polyol, and forming oxides of the metal on the catalyst composite.

2. The process of claim 1 wherein the impregnation is via incipient wetness.

3. The process of claim 1 wherein the catalytic metal, or metals, and the polyol are codeposited onto the support from a single impregnating solution.

4. The process of claim 1 wherein the catalytic metal, or metals, impregnated onto the support comprises copper or an Iron Group Metal.

5. The process of claim 1 wherein the support is contacted with a solution which contains, in addition to a) a compound, or salt, of a catalytic metal, or metals, and b) a polyol as described in said claim 1, c) a compound, or salt, of rhenium.

6. The process of claim 5 wherein the catalytic metal, or metals, rhenium, and the polyol are codeposited from a single solution onto the support via incipient wetness, the catalytic metal, or metals, comprises copper or an Iron Group metal, and the polyol has the formula $HOCH_2-(CHOH)_{n'}-CH_2OH$ wherein n' is an integer defining the number of CHOH groups, and ranges from 0 to about 4.

7. The process of claim 6 wherein the Iron Group metal is cobalt, and n' of the polyol formula ranges from about 2 to about 4.

8. The process of claim 5 wherein the rhenium is added to the support in concentration sufficient to provide a weight ratio of elemental rhenium:copper or Iron Group metal ranging from about 0.005:1 to about 0.2:1.

9. The process of claim 8 wherein the weight ratio of elemental rhenium: copper or Iron Group metal ranges from about 0.01:1 to about 0.1:1.

10. The process of claim 5 wherein, after drying, the catalyst is calcined and reduced.

11. The process of claim 1 wherein the compound, or salt of the catalytic metal comprises cobalt, the impregnating solution contains additonally (c) a compound, or salt, of rhenium, and the impregnated support is titania or silica.

12. A catalyst useful for the hydrogenation of carbon monoxide formed by the steps comprising
    impregnating a refractory inorganic oxide support with a solution which contains
    a) a compound, or salt, or a catalytic metal, or metals,
    b) a polyol having the following empirical formula $C_n H_{2n+2} O_x$ where n is an integer ranging from 2 to about 6, and x is an integer ranging from 2 to n, sufficient to disperse the compounds or salt of the catalytic metal, or metals, onto the support,
    drying, and removing the polyol, and forming oxides of the metal on the catalyst composite.

13. The composition of claim 12 wherein the support is contacted with a solution which contains, in addition to a) a compound, or salt, of a catalytic metal, or metals, and b) a polyol as described in said claim 12, c) a compound, or salt, of rhenium.

14. The composition of claim 13 wherein the catalytic metals, or metals, comprises copper or an Iron Group metal, and rhenium is contained on the support in weight ratio of elemental rhenium:copper or Iron Group metal ranging from about 0.005:1 to about 0.2:1.

15. The composition of claim 14 wherein the catalytic metal impregnated with rhenium onto the support is cobalt, and the support is titania or silica.

16. A process for the production of $C_5+$ liquid hydrocarbons from a hydrogen and carbon monoxide synthesis gas by contact of said gas with the catalyst of claim 12 at reaction conditions.

17. The process of claim 16 wherein the support is contacted with a solution which contains, in addition to a) a compound, or salt, of a catalytic metal, or metals, and b) a polyol, c) a compound, or salt, of rhenium.

18. The process of claim 17 wherein the catalytic metal impregnated with rhenium onto the support is cobalt, and the support is titania or silica.

19. The process of claim 16 wherein at least a portion of the $C_5+$ liquid hydrocarbon is converted and upgraded.

20. The process of claim 19 wherein the conversion is effected through hydrotreating.

* * * * *